(12) United States Patent
Itoi et al.

(10) Patent No.: US 8,298,520 B2
(45) Date of Patent: Oct. 30, 2012

(54) DEODORANT PARTICLE

(75) Inventors: Takashi Itoi, Tochigi (JP); Koji Mimura, Tochigi (JP); Daisuke Yamazaki, Wakayama (JP); Masafumi Miyamoto, Wakayama (JP); Tetsuji Kito, Wakayama (JP); Seiichi Miyanaga, Tokyo (JP); Hirohiko Ishida, Tokyo (JP)

(73) Assignee: Kao Corporation, Tokyo (JP)

( * ) Notice: Subject to any disclaimer, the term of this patent is extended or adjusted under 35 U.S.C. 154(b) by 745 days.

(21) Appl. No.: 12/227,307

(22) PCT Filed: Jun. 27, 2007

(86) PCT No.: PCT/JP2007/062942
§ 371 (c)(1),
(2), (4) Date: Nov. 13, 2008

(87) PCT Pub. No.: WO2008/007557
PCT Pub. Date: Jan. 17, 2008

(65) Prior Publication Data
US 2009/0238847 A1    Sep. 24, 2009

(30) Foreign Application Priority Data

| Jul. 14, 2006 | (JP) | 2006-193643 |
| Aug. 10, 2006 | (JP) | 2006-218774 |
| Aug. 10, 2006 | (JP) | 2006-218775 |
| Oct. 5, 2006 | (JP) | 2006-273682 |

(51) Int. Cl.
*A61L 9/01* (2006.01)
*A61K 9/00* (2006.01)
*C08F 2/00* (2006.01)

(52) U.S. Cl. .......... 424/76.1; 424/400; 526/72
(58) Field of Classification Search .......... 424/400, 424/76.1; 526/72
See application file for complete search history.

(56) References Cited

U.S. PATENT DOCUMENTS
4,186,076 A    1/1980    de Nora et al.
(Continued)

FOREIGN PATENT DOCUMENTS
JP    54-128981 A    10/1979
(Continued)

OTHER PUBLICATIONS

Extended European Search Report issued Aug. 25, 2010, in EP 07767740.9.
(Continued)

*Primary Examiner* — Blessing Fubara
(74) *Attorney, Agent, or Firm* — Birch, Stewart, Kolasch & Birch, LLP

(57) ABSTRACT

Disclosed is a deodorant particle having a BET specific surface area of 10 m²/g or more that are obtained by copolymerizing a monomer system including a crosslinkable vinyl monomer and a vinyl monomer having a heteroaromatic ring. The deodorant particles may contain a metal ion. Also disclosed is a process of producing the deodorant particles including the step of copolymerizing a monomer system containing a crosslinkable vinyl monomer and a vinyl monomer having a heteroaromatic ring by oil-in-water emulsion polymerization or precipitation polymerization using an organic solvent whose solubility parameter is different from that of the monomers by an absolute difference of 0 to 2.0. The process can further include the step of bringing the particles obtained by the polymerization into contact with a solvent having a metal salt dissolved therein to support a metal ion on the particle.

9 Claims, 3 Drawing Sheets

U.S. PATENT DOCUMENTS

| | | | |
|---|---|---|---|
| 4,594,392 A | 6/1986 | Hatch | |
| 2004/0024104 A1* | 2/2004 | Ota et al. | 524/492 |

FOREIGN PATENT DOCUMENTS

| | | | |
|---|---|---|---|
| JP | 62-286905 A | | 12/1987 |
| JP | 1-245859 A | | 10/1989 |
| JP | 2-300379 A | | 12/1990 |
| JP | 3-213562 A | | 9/1991 |
| JP | 9-188778 A | | 7/1997 |
| JP | 2587377 Y2 | | 12/1998 |
| JP | 11-147915 A | | 6/1999 |
| JP | 2001-70339 A | | 3/2001 |
| JP | 2001070339 | * | 3/2001 |
| JP | 2003-52746 A | | 2/2003 |
| JP | 2005-076145 A | | 3/2005 |
| JP | 2005-76145 A | | 3/2005 |
| JP | 2005076145 | * | 3/2005 |
| JP | 2005-344066 A | | 12/2005 |

OTHER PUBLICATIONS

Itabashi et al., "Study on Utilization of Natural Zeolite (II) Chemical Modification of Natural Zeolite", Aist Tohoku, Nov. 28, 2004, pp. 47-54, XP002592550; retrieved from Internet: URL:http://unit.aist.go.jp/tohoku/techpaper/pdf/6518.pdf.

"Study of Effect on High Molecule Absorbent to Adsorption Selectivity of Each Glucoside in Stevia Rebaudiana Bertoni," Science in China (Series B), Dec. 31, 1998.

Chinese Office Action mailed on Feb. 18, 2011 in corresponding Chinese Patent Application No. 200780019632.6 with its English translation.

Ma et al., "Study on the Synthesis and Properties of S-Naproxen Molecularly Imprinted Polymers Usinig N-vinylpyrrolidone as a Functional Monomer," Journal of Functional Polymers, vol. 18, No. 1, pp. 15-19, Mar. 31, 2005.

Office Action issued Mar. 25, 2010 in Chinese Patent Application No. 200780019832.6.

European Office Action for Application No. 07767740.9, dated May 24, 2011.

Japanese Notice of Rejection dated Oct. 11, 2011, issued in connection with Japanese Application No. 2007-168521.

Japanese Notice of Rejection dated Oct. 4, 2011, issued in connection with Japanese Application No. 2007-168508.

* cited by examiner

DEODORANT PARTICLE

TECHNICAL FIELD

The present invention relates to deodorant particles having high deodorizing performance including odor removing and odor-preventive properties and a process of producing the same. The present invention also relates to a deodorant fibrous product that is a fibrous product with deodorizing performance. The invention furthermore relates to an absorbent article having deodorizing effects.

BACKGROUND ART

Use of deodorants based on activated carbon, silica, activated alumina, sepiolite, or aluminosilicates, such as natural or synthetic zeolite, has been known usually as a means to remove malodors. However, many of such solid deodorants are effective only on specific odors such as acidic or basic odors and cannot be said to have sufficient deodorizing effects. This is because a malodor is not something from a single substance but a composite odor of many malodorous compounds. Few deodorants showing broad deodorization spectrum have been proposed, and, if any, the conditions of their usage have been limited.

Patent Document 1 (see below) discloses porous, crosslinked polymer particles prepared from an aromatic polyvinyl compound and an aromatic monovinyl compound, suggesting utility as an organic matter adsorbent. However, the publication is silent on adsorption of malodorous components. The particles disclosed have insufficient performance as a deodorant.

Patent Document 2 discloses polymer particles containing a metal component, which are obtained by having fine metal particles supported on a porous polymer body thereby endowing the polymer particles with functions essentially possessed by the metal particles such as antibacterial, odor-preventive effects. However, the technique proposed requires a reducing agent for reducing a metal salt, which incurs high cost. Another disadvantage of the technique is that the ligand of the metal salt becomes useless after reducing the metal salt to metal. Although the publication recites a carboxyl group, a sulfonic acid group, an amino group, etc. as an ion-exchangeable or ion-coordinable polar group, it does not refer to the high metal supporting ability by a heteroaromatic ring.

Patent Document 3 discloses a porous ion-exchange resin obtained by crosslinking polymerization of a metal complex having a polymerizable functional group as a ligand but has no mention of its deodorizing ability. Additionally, the process proposed is inefficient because it allows a metal component to be incorporated into the inside of the polymer, resulting in reduction of the metal component distribution on the surface of the polymer particles or pores as compared with addition of a metal salt to porous polymer particles to have the metal ion supported thereon.

Deodorant absorbent articles, such as disposable diapers, having an absorbent member wrapped in a deodorant fibrous sheet (deodorant fibrous product) to seal in the odor of excreta have been proposed as disclosed, e.g., in Patent Document 4. The deodorant fibrous product disclosed in Patent Document 4 is a fibrous material having adhered thereto a deodorizing agent having pores with a specific opening size in a specific volumetric proportion. While the deodorant fibrous product of Patent Document 4 exhibits a considerable deodorizing effect, there still is a demand for deodorant fibrous products with further improved deodorizing performance.

[Patent Document 1] JP 11-147915A
[Patent Document 2] JP9-188778A
[Patent Document 3] JP1-245859A
[Patent Document 4] JP2001-70339A

DISCLOSURE OF THE INVENTION

The present invention provides a deodorant particle having a BET specific surface area of 10 $m^2/g$ or more that is obtainable by copolymerizing monomers comprising a crosslinkable vinyl monomer and a vinyl monomer having a heteroaromatic ring.

The present invention also provides a process of producing the above-mentioned deodorant particle including the step of copolymerizing monomers including a crosslinkable vinyl monomer and a vinyl monomer having a heteroaromatic ring by oil-in-water emulsion polymerization or precipitation polymerization using an organic solvent whose solubility parameter is different from that of the monomers by an absolute difference of 0 to 2.0. The process may further include the step of bringing the particles obtained by the polymerization into contact with a solvent having a metal salt dissolved therein to support a metal ion on the particle.

DETAILED DESCRIPTION OF THE INVENTION

Figure 1:
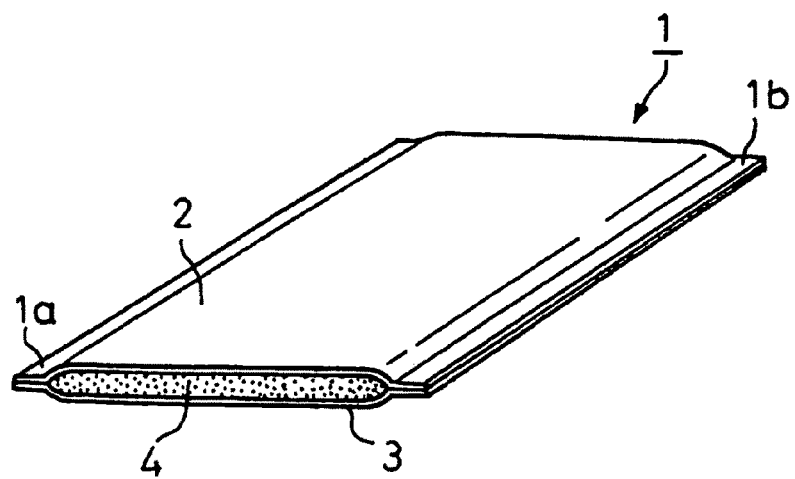
FIG. 1 is a perspective of a particle-containing sheet which is an embodiment of the deodorant fibrous product of the present invention.

The present invention provides deodorant particles exhibiting excellent deodorizing performance on not only acidic and basic odors but neutral to weakly acidic odors typified by phenols and sulfides, especially on composite odors such as human or animal (cats and dogs) urine and feces odors, tobacco odor, etc.

As a result of extensive investigations, the present inventors have found that porous polymer particles obtained by copolymerizing a monomer system containing a crosslinkable vinyl monomer and a vinyl monomer having a heteroaromatic ring are superior deodorant particles having a broad deodorization spectrum based on physical adsorption taking full advantage of their large specific surface area. They have also found that the polymer particles having a metal salt coordinated to the heteroaromatic ring thereof exhibit further enhanced deodorizing effects on sulfides, ammonia, amines, and fatty acids through chemical adsorption.

The deodorant particle of the present invention is obtained by copolymerizing monomers containing a crosslinkable vinyl monomer and a vinyl monomer having a heteroaromatic ring.

The crosslinkable vinyl monomer is a monomer having two or more vinyl groups. Examples of the crosslinkable vinyl monomer include divinylbenzene, trivinylbenzene, and ethylene glycol di(meth)acrylate, with divinylbenzene being preferred. The larger the proportion of the crosslinkable vinyl monomer in the monomer system, the larger the BET specific surface area of the resulting polymer particles. Accordingly, the proportion of the crosslinkable vinyl monomer in the monomer system (total monomer) is preferably 5% by mass or more, more preferably 20% by mass or more, even more preferably 50% by mass or more. The upper limit of the proportion is preferably 98%, more preferably 90%, by mass.

The vinyl monomer having a heteroaromatic ring is not particularly limited as long as it has a vinyl group and a heteroaromatic ring. As used herein the term "heteroaromatic ring" refers to the ring of an organic cyclic compound containing a hetero atom such as oxygen, sulfur or nitrogen in addition to a carbon atom as a ring member. Examples of the heteroaromatic ring include those having one nitrogen atom, such as a pyridine, pyrrole, and quinoline ring; those having two nitrogen atoms, such as an imidazole, a pyrimidine, a pyrazine, and a pyrazole ring; those having a sulfur atom, such as a thiophene and a thiazole ring; and those having an oxygen atom, such as a furan ring. It is considered that the lone electron pair of the hetero atom enhances adsorption of malodorous substances and also participate in chemical bonding of metal ions hereinafter described. Preferred of the recited heteroaromatic rings are a pyridine, an imidazole, and a pyrimidine ring. Examples of vinyl monomers having a heteroaromatic ring are 2-vinylpyridine, 4-vinylpyridine, I-vinylimidazole, and 2-vinylpyrimidine, with 2-vinylpyridine and 4-vinylpyridine being preferred.

It is preferred that the monomer system contain the vinyl monomer having a heteroaromatic ring in a sufficient proportion so that the deodorant polymer may adsorb malodorous components sufficiently and hold a sufficient amount of a metal salt. Specifically, the proportion of the vinyl monomer having a heteroaromatic ring in the monomer system is preferably 1% or more, more preferably 2% or more, even more preferably 4% or more, by mass. When it is desired to ensure absorptivity by increasing the BET specific surface area of the deodorant particles, the proportion of the vinyl monomer having a heteroaromatic ring in the monomer system is preferably 50% or less, more preferably 30% or less, by mass.

In the present invention, the monomer system from which the deodorant polymer is prepared may further contain other monomers copolymerizable with the crosslinkable vinyl monomer and the vinyl monomer having a heteroaromatic ring, such as aromatic vinyl monomers, unsaturated acid esters, and unsaturated acids. Examples of useful aromatic vinyl monomers include styrene, α-methylstyrene, vinyltoluene, ethylvinylbenzene, and vinylbenzyl chloride. Examples of useful unsaturated acid esters include methyl (meth)acrylate, ethyl (meth)acrylate, propyl (meth)acrylate, butyl (meth)acrylate, 2-ethylhexyl (meth)acrylate, cyclohexyl (meth)acrylate, benzyl (meth)acrylate, and glycidyl (meth) acrylate. Examples of useful unsaturated acids include (meth) acrylic acid. Acrylonitrile and methacrylonitrile are also usable. The aromatic vinyl monomers are preferred of them, with styrene being particularly preferred.

The terms "(meth)acrylic acid" and "(meth)acrylate" as used herein mean acrylic acid or methacrylic acid, and acrylate or methacrylate, respectively.

The BET specific surface area of the deodorant particles of the present invention can freely be adjusted by appropriate selection of the proportion of the crosslinkable vinyl monomer and the kind of the organic solvent used in polymerization. Considering that deodorant particles with a larger BET specific surface area exhibit a higher physical deodorizing effect, the particles should have a BET specific surface area of 10 $m^2/g$ or more, preferably 50 $m^2/g$ or more, even more preferably 200 $m^2/g$ or more, most preferably 300 $m^2/g$ or more. The upper limit of the BET specific surface area, while not critical, is preferably 800 $m^2/g$. The BET specific surface area as referred to herein is a value measured by the BET one-point method described in Example given later.

The particle size of the deodorant particles is not particularly limited and may be selected as appropriate to the type of the deodorant product to which the particles are applied. For example, granular particles of about 0.1 to 5 mm in diameter are suitably placed in an air permeable container or the like to provide a deodorant product with high deodorizing performance. Powder having a particle size of about 0.1 to 100 μm also works. Powder of 0.1 to 10 μm in particle size is preferred because it is easy to use combinedly with other materials, for example, when kneaded with a resin or dispersed in a liquid.

The deodorant particles used in the invention are preferably prepared by oil-in-water emulsion polymerization or precipitation polymerization.

In the case of oil-in-water emulsion polymerization, a monomer system including the crosslinkable vinyl monomer and the vinyl monomer having a heteroaromatic ring is mixed with an organic solvent, a surface active agent, water, and, if necessary, a polymerization initiator to prepare an oil-in-water emulsion, which is heated to induce polymerization. The polymer thus produced separates from the organic solvent phase. The reaction system is filtered, and the filter cake is freed of water and the surface active agent and dried to remove the organic solvent to give porous deodorant particles.

In the case of precipitation polymerization, a monomer system including the crosslinkable vinyl monomer and the vinyl monomer having a heteroaromatic ring is mixed with an organic solvent and, if necessary, a polymerization initiator to prepare a solution, which is heated to induce polymerization to precipitate polymer particles. The reaction system is dried to remove the organic solvent to give porous deodorant particles.

Organic solvents that can be used in the oil-in-water emulsion polymerization include aromatic compounds, aliphatic hydrocarbons, and alcohols. Examples of suitable organic solvents are benzene, toluene, xylene, ethylbenzene, o-dichlorobenzene, hexane, heptane, octane, isooctane, decane, cyclohexane, n-butanol, t-butanol, and 1-hexanol. Heptane, octane, and toluene are preferred. These solvents can be used either individually or as a mixture thereof. The organic solvent is used in an amount preferably of 5% by mass or more, more preferably 25% by mass or more, based on the total monomer mass in order to secure a sufficient specific surface area of the resulting particles. The upper limit of the amount of the solvent is preferably 300% by mass, more preferably 150% by mass, based on the total monomer mass in order to secure a satisfactory rate of polymerization.

Organic solvents that can be used in the precipitation polymerization include those recited above for use in the oil-in-water emulsion polymerization. In addition thereto, highly water soluble alcohols, such as methanol, ethanol, 1-propanol, isopropyl alcohol, and methyl isobutyl carbinol, can be used either alone or in combination with other organic solvent so that the absolute difference in solubility parameter between the solvent (including a mixed solvent system) and the monomer system may fall within a range of from 0 to 2.0. The amount of the organic solvent to be used is preferably not less than 100% by mass, more preferably not less than 200% by mass, based on the total monomer mass so as not to result in production of particles with a reduced specific surface area and so as to facilitate uniform stirring of the solution while preventing the solution from gelling. To secure a sufficient rate of polymerization, the upper limit of the amount of the solvent is preferably 1000% by mass, more preferably 500% by mass, based on the total monomer mass.

In order to obtain deodorant particles with a sufficient BET specific surface area by oil-in-water emulsion polymerization or precipitation polymerization, it is desirable that the difference in solubility parameter between the monomer system and the organic solvent be small enough. The term "solubility parameter" as used herein is a value calculated by Fedors' method (R. F. Fedors, *Polymer Engineering and Science*, Vol. 14, p. 147 (1974)) and expressed in units of $(cal/cm^3)^{1/2}$. Solubility parameter is one of measures representing affinity between a monomer system and an organic solvent. A smaller solubility parameter difference indicates a higher affinity.

More specifically, a solubility parameter δ of a monomer is determined by obtaining an energy of vaporization ΔE and a molar volume V of the atomic group constituting the molecule and calculating according to equation:

$$\delta = (\Delta E/V)^{1/2} (cal/cm^3)^{1/2}$$

In the case of a monomer mixture composed of two or more monomers, a solubility parameter $\delta_{mix}$ of the mixture is obtained from the solubility parameter δi of each monomer and the volume fraction ϕ of each monomer according to equation:

$$\delta_{mix} = \Sigma \delta_i \phi_i (cal/cm^3)^{1/2}$$

Too large a difference between the monomer system and the organic solvent in solubility parameter results in a considerably reduced BET specific surface area of the resultant polymer particles. It is therefore preferred that the absolute difference in solubility parameter between the monomer system and the organic solvent be in the range of from 0 to 2.0 in order to obtain deodorant polymer particles with a large BET specific surface area. More preferably, the absolute solubility parameter difference is or smaller. In cases where the particles are produced by oil-in-water emulsion polymerization, there is not a particular lower limit to the solubility parameter difference. In the case of precipitation polymerization, the absolute solubility parameter difference is preferably 0.5 or greater, more preferably 1.0 or greater.

Any surface active agent can be used in the oil-in-water emulsion polymerization as long as it is capable of forming a stable oil-in-water emulsion from a mixture of water and the monomer system comprising a crosslinkable vinyl monomer and a vinyl monomer having a heteroaromatic ring. Suitable surface active agents include anionic ones such as dodecylsulfates, dodecylbenzenesulfonates, N-stearyltaurates, and polyoxyethylene nonylphenyl ether sulfates; and nonionic ones such as polyoxyethylene nonylphenyl ether, polyoxyethylene dodecylphenyl ether, sorbitan monostearate, polyoxyethylene sorbitan monostearate, and polyvinyl alcohol. Sodium N-stearyltaurate or polyvinyl alcohol is preferred. The amount of the surface active agent is not particularly limited as long as the oil-in-water emulsion state is stable. The amount is preferably 0.01% to 3% by mass, more preferably 0.1% to 1% by mass, based on the water.

The polymerization initiator thermally decomposes to produce free radicals to initiate addition polymerization of the monomers. Examples of initiators generally employed include oil-soluble peroxodisulfates, peroxides, and azobis compounds.

The deodorant particles that can be used in the present invention preferably contain a metal ion. Metal ions can be supported on the surfaces of the pores of the deodorant particles through coordination bonding to the heteroaromatic rings existing on the polymer surface. Malodorous gases such as ammonia, amines, sulfides, and fatty acids are adsorbed through coordination bonding to the metal ions supported on the deodorant particles. That is, the deodorant particles having metal ions supported thereon show markedly enhanced deodorizing performance owing to the physical deodorizing function attributed to the large BET specific surface area and the chemical deodorizing function attributed to the supported metal ions.

Examples of the metal ion include a silver, a zinc, an aluminum, a cobalt, a zirconium, a cerium, an iron, a copper, a nickel, and a platinum ion, with a silver and a zinc ion being preferred.

The deodorant particles having a metal ion supported thereon is obtainable by bringing the slurry after the polymerization reaction or the particles after drying and solvent removal into contact with a solvent having a metal salt dissolved therein. Where necessary, the contact is carried out while heating at 30° to 80° C. The amount of the metal ion to be supported is preferably 0.01% or more, more preferably 0.1% or more, by mass based on the polymer particles. The upper limit of the amount, while not critical, is preferably 10%, more preferably 5%, by mass.

Any salt of the metal can be used to supply desired metal ions to the deodorant particles as long as it is soluble in water or an organic solvent. Examples of suitable metal salts are silver nitrate, aluminum nitrate, cobalt nitrate, zirconium nitrate, cerium nitrate, iron (II) nitrate, iron (III) nitrate, copper nitrate, nickel nitrate, silver acetate, cerium chloride, iron (II) chloride, iron (III) chloride, zinc chloride, copper chloride, silver perchlorate, aluminum perchlorate, platinum perchlorate, zinc perchlorate, zirconium perchlorate, silver sulfate, aluminum sulfate, copper sulfate, and zinc sulfate. These metal salts may be used either individually or as a combination of two or more thereof. Silver nitrate, silver acetate, and zinc chloride are particularly preferred.

Any solvent can be used to dissolve the metal salt as long as the metal salt dissolves and the deodorant particles uniformly disperse therein. Examples of suitable solvents are water, diethyl ether, acetone, and alcohols (e.g., methanol, ethanol, 1-propanol, 2-propanol, and glycerol). They can be used either individually or as mixture thereof.

The deodorant particles of the present invention are useful in a wide variety of applications as a deodorizer in deodorant products for domestic use that are designed to remove various malodors generated in daily life and deodorant products for commercial or industrial use. Products designed to remove various malodors generated in daily life include disposable diapers, incontinence products, feminine hygiene products including sanitary napkins and panty liners, air fresheners such as sprays (including aerosol, trigger and pump types), deodorant products to be placed at a fixed location on demand (including gels, solutions, and sheets), cleaning sheets (wet or dry), body deodorants (including aerosols, sticks, roll-ons, and pump sprays), deodorant sprays for pets (including aerosol and trigger types), pet excreta treating products in the form of a sheet or pellets, laundry detergents, fabric softeners, fabric conditioners, and hair sprays. Deodorant products for commercial or industrial use include air freshener sprays for improving the working environment in or around a factory, deodorizing devices, filters of air conditioners, fibers, wall papers, carpets, clothing such as shirts and socks, and water purifiers.

According to the present invention, a deodorant fibrous product comprising the deodorant particles is also provided. The deodorant fibrous product of the invention is a fibrous material having deodorant particles adhered thereto. Suitable fibrous materials include cellulosic fibers such as pulp and rayon. The cellulosic fiber may be used in combination with a small proportion of heat fusible fiber made from thermoplastic resins.

The deodorant fibrous product according to the present invention takes various forms depending on the method of making, including sheets, broken pieces of sheets, granules, and three-dimensional moldings. The deodorant fibrous products of such forms can be produced by, for example, a wet papermaking technique. The deodorant fibrous product of sheet form may be a single ply sheet containing the deodorant particles or a laminate sheet composed of a plurality of sheets. In the former case, the sheet is preferably produced by wet papermaking using a slurry containing a fibrous material and the deodorant particles. The single ply sheet may be a nonwoven fabric made, e.g., of thermoplastic fiber having the deodorant particles supported thereon.

The deodorant fibrous product of laminate sheet form is exemplified by the sheet illustrated in FIG. 1. The deodorant fibrous product of FIG. 1 is a laminate sheet composed of two rectangular pulp sheets of a size (a first pulp sheet 2 and a second pulp sheet 3) and a rectangular inner sheet 4 interposed between the pulp sheets 2 and 3. The inner sheet 4 is the same as the above-described single ply sheet. The inner sheet 4 has a smaller width than the pulp sheets 2 and 3 and is held between the laterally middle portions of the two pulp sheets 2 and 3. The inner sheet 4 and the pulp sheets 2 and 3 are integrated by successively feeding the respective stocks to a paper machine.

The inner sheet 4 is absent in the lateral side portions 1a and 1b of the deodorant fibrous product 1. Namely, the lateral side portions 1a and 1b each have a double ply structure composed of the pulp sheets 2 and 3. With both the side portions of the deodorant fibrous product 1 sealed by joining the pulp sheets 2 and 3 along their lateral side portions, the deodorant particles are prevented from falling off from the side edges of the product 1. The width of the side portions 1a and 1b is preferably 0.1 to 20 cm, more preferably 1 to 6 cm, to secure prevention of the deodorant particles' failing off and to fulfill the full function of the deodorant particles.

As previously stated, a fibrous material of sheet form having the deodorant particles adhered thereto, i.e., the above-described single ply sheet or the inner sheet 4 is produced by a wet papermaking technique using a slurry containing the fibrous material and the deodorant particles. A flocculant may be added to the slurry to increase the amount of the deodorant particles adhered to the fibrous material. Polyacrylamide is an example of preferred flocculants. The slurry preferably contains the deodorant particles in an amount of 0.1 to 50 parts by mass, more preferably 0.5 to 30 parts by mass, per 100 parts by mass of the fibrous material. The slurry preferably contains the fibrous material in a concentration of 0.5% to 5.0% by mass, more preferably 1.0% to 3.0% by mass.

The sheet obtained by a wet papermaking technique (i.e., the above-described single ply sheet or inner sheet 4) preferably contains 0.1% by mass or more, more preferably 0.5% by mass or more, still preferably 2% by mass or more, of the deodorant particles. The upper value of the content of the deodorant particles is not limited. From the economical viewpoint, the sheet preferably contains 30% by mass or less of the deodorant particles. The grammage of the sheet, while varying depending on the intended use, is preferably 10 to 100 $g/m^2$, more preferably 10 to 50 $g/m^2$.

The deodorant fibrous product of sheet form may be cut or broken into small pieces for use as another form of the deodorant fibrous product.

As previously described, the deodorant fibrous product of the present invention may take various forms other than the sheet form, such as granules or three-dimensional moldings. A granular deodorant fibrous product can be obtainable by extruding a high concentration slurry of a fibrous material containing the deodorant particles from an extruder into strands, which are chopped into pellets. Examples of the three-dimensional moldings as a deodorant fibrous product include containers such as bottles, cups, and trays. Such three-dimensional moldings are conveniently produced by a pulp molding method. For the details of a pulp molding method, reference can be made to it, e.g., in WO99/42661.

The deodorant fibrous products according to the present invention produce deodorizing (removal of odors of urine, excrement, vaginal discharges and menstrual blood, and other odors of putrefaction) and antibacterial effects. Applications of the deodorant fibrous products of sheet form or in the form of broken pieces of a sheet include wallpaper, bed sheets, closet liners, drawer liners, shoe cupboard liners, mats, insoles, masks, filters, and underlays for wrapping foods. The deodorant fibrous products of sheet form can be turned into disposable undergarments or clothes. They are also useful as a toilet wipe formed of nonwoven fabric containing a cleaning agent and deodorant particles or as a deodorant filter. The deodorant fibrous products of granular form such as beads or pellets are useful as, for example, pet deodorizers such as cat litter. The deodorant fibrous products of three-dimensional shape are useful as, for example, antimicrobial deodorant boxes.

The method of producing the deodorant fibrous product is not limited to the above-mentioned wet papermaking technique. For example, a liquid containing the deodorant particles is sprayed onto a dry-processed fibrous product and dried, or the deodorant particles are mixed with or held by a fibrous material while the fibrous material is being dry-processed into a fibrous product, thereby to provide the deodorant fibrous product of the invention. The deodorant fibrous product of the invention may also be produced by compression extrusion of a mixture of the deodorant particles and fibers including heat fusible fiber.

According to the present invention, an absorbent article comprising the deodorant particles is also provided. It is advantageous that the deodorant particles contain the above-mentioned metal ion. As used herein the term "absorbent article" refers to devices that absorb and retain body exudates, mostly urine or menstrual blood, including but not limited to disposable diapers, incontinence pads, and sanitary napkins.

The absorbent article of the present invention typically includes a topsheet, a backsheet, and a liquid retentive absorbent member interposed between the topsheet and the backsheet. The topsheet and the back sheet can be of any materials that have been commonly employed in the art. For example, liquid permeable sheets including various types of hydrophilized nonwoven fabrics and perforated resin films can be used as the topsheet. Liquid impermeable or repellent sheets, such as thermoplastic resin films and their laminates with nonwoven fabric, can be used as the backsheet. The backsheet may have moisture permeability. The absorbent article may optionally have other various members as appropriate for the intended use. Such members are well known to those skilled in the art. For example, disposable diapers and sanitary napkins may have a pair of standing cuffs in laterally opposing side portions thereof.

The configuration of the absorbent article having the deodorant particles is not particularly limited. Taking for instance an absorbent article having the above-described typical structure composed of a topsheet, a backsheet, and an absorbent member interposed therebetween, preferred, however, are (a) a configuration in which the deodorant particles are supported directly on the fibers constituting the absorbent member and (b) a configuration in which a particle-containing sheet formed by adhering the deodorant particles to a fibrous material is disposed between the topsheet and the absorbent member, or within the absorbent member, or between the absorbent member and the backsheet.

The configuration (a) is obtained by, for example, spreading the deodorant particles over an aggregate of fibers constituting an absorbent member, such as a web of staple fibers or continuous fibers, and wrapping the fiber aggregate with the particles in paper. The constituent fibers may further have a superabsorbent polymer supported thereon. In that case, it is advantageous that the deodorant particles and the superabsorbent polymer are premixed, and the mixed particles are spread over the fiber aggregate. The deodorant particles may previously be adhered to the superabsorbent polymer to prepare composite particles, which are spread over a fiber aggregate. The amount of the deodorant particles to be incorporated into the absorbent article is not particularly limited. Taking for instance an absorbent article designed to absorb 100 ml of urine, a recommended amount is 40 mg or more per article.

The fibrous material of the particle-containing sheet used in the configuration (b) is preferably one which can be made into a fibrous sheet by a wet papermaking technique. Examples of such a fibrous material include cellulosic fibers such as pulp and rayon. A small proportion of heat fusible fibers made from thermoplastic resins may be used in combination.

The particle-containing sheet used in the configuration (b) may be a single ply sheet containing the deodorant particles or a laminate sheet composed of a plurality of sheets containing the deodorant particles. In the former case, the sheet is produced by, for example, wet papermaking using a slurry containing the fibrous material and the deodorant particles.

The particle-containing sheet of laminate form is exemplified by the above-mentioned deodorant fibrous product illustrated in FIG. 1.

Figure 2:
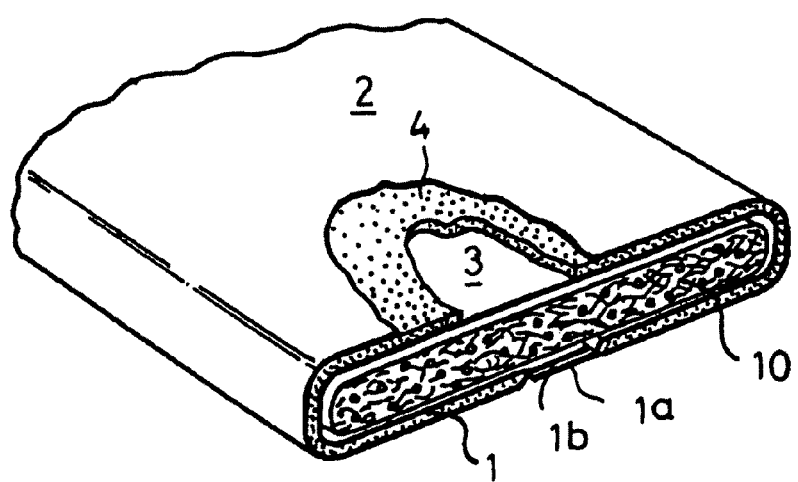
FIG. 2 is a fragmentary perspective of an absorbent member wrapped in the particle-containing sheet of FIG. 1.
Figure 3:
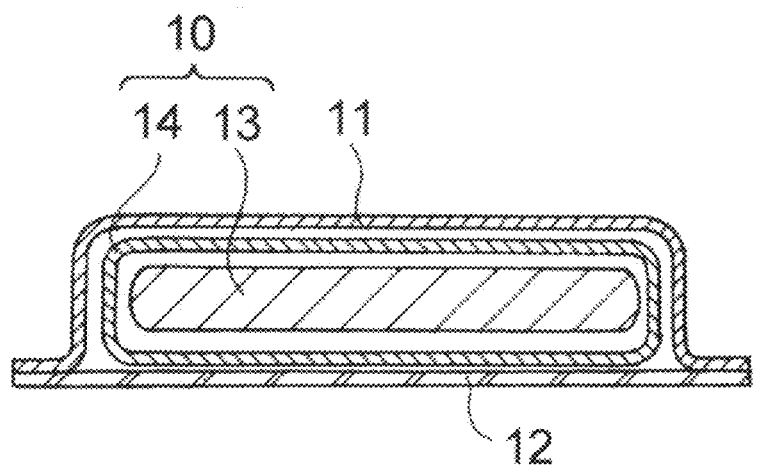
FIG. 3 is a cross-section of an absorbent article made in Example 16-1, taken in the lateral direction.

The particle-containing sheet can be disposed, for example, between a liquid permeable topsheet and a liquid retentive absorbent member, within an absorbent member, or between an absorbent member and a liquid impermeable or repellent backsheet. FIG. 2 illustrates an absorbent member 10 wrapped in the deodorant fibrous product 1 having a laminate structure shown in FIG. 1. The particle-containing sheet may be a single ply sheet. The absorbent member 10 is composed of pulp fiber and superabsorbent polymer particles. The particle-containing sheet 1 wraps around the absorbent member 10 and meets itself with its opposite side portions 1a and 1b overlapping each other. The absorbent member 10 as wrapped in this way is held between a topsheet (not shown) and a backsheet (not shown). Thus, in the embodiment shown in FIG. 2, the deodorant fibrous product 1 is disposed between the topsheet and the absorbent member 10 and also between the absorbent member 10 and the backsheet.

Figure 5:
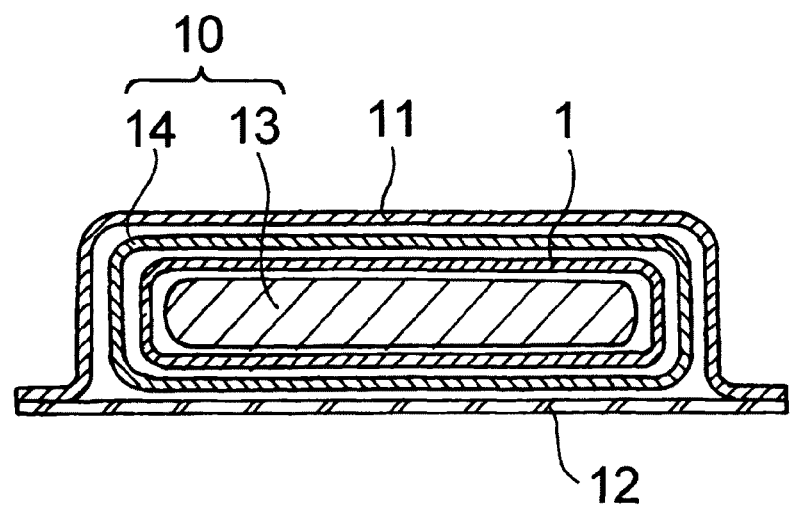
FIG. 5 is a cross-section of an absorbent article made in Example 18-1, taken in the lateral direction.

The deodorant fibrous product 1 may be disposed within the absorbent member as a part of it. Specifically, when an absorbent member 10 is composed of a fiber aggregate 13 and a wrapping paper 14, the deodorant fibrous product 1 may wrap the fiber aggregate 13 and be wrapped in the wrapping paper 14 as illustrated in FIG. 5. The absorbent member 10 is held between the topsheet 11 and the backsheet 12.

EXAMPLES

In Examples hereinafter given, all the parts and percents are by weight unless otherwise noted. The solubility parameters are given in units of $(cal/cm^3)^{1/2}$.

Example 1

In a mixed organic solvent of 200 g of heptane and 100 g of toluene were dissolved 100 g of a monomer mixture (styrene/divinylbenzene/2-vinylpyridine=35/60/5) and 3 g of lauroyl peroxide in a polymerization vessel. The solubility parameters of the monomer mixture and the organic solvent were 9.28 and 7.88, respectively, making a difference of 1.44. The monomer mixture was heated at 70° C. for 8 hours and then at 80° C. for 8 hours to conduct polymerization and then dried to give deodorant particles in a yield of 88%.

Example 2

In a mixed organic solvent of 200 g of heptane and 100 g of toluene were dissolved 100 g of a monomer mixture (styrene/divinylbenzene/2-vinylpyridine=25/70/5) and 3 g of lauroyl peroxide in a polymerization vessel. The solubility parameters of the monomer mixture and the organic solvent were 9.29 and 7.88, respectively, making a difference of 1.41. The monomer mixture was heated at 70° C. for 8 hours and then at 80° C. for 8 hours to conduct polymerization and then dried to give deodorant particles in a yield of 90%.

Example 3

Figure 4:
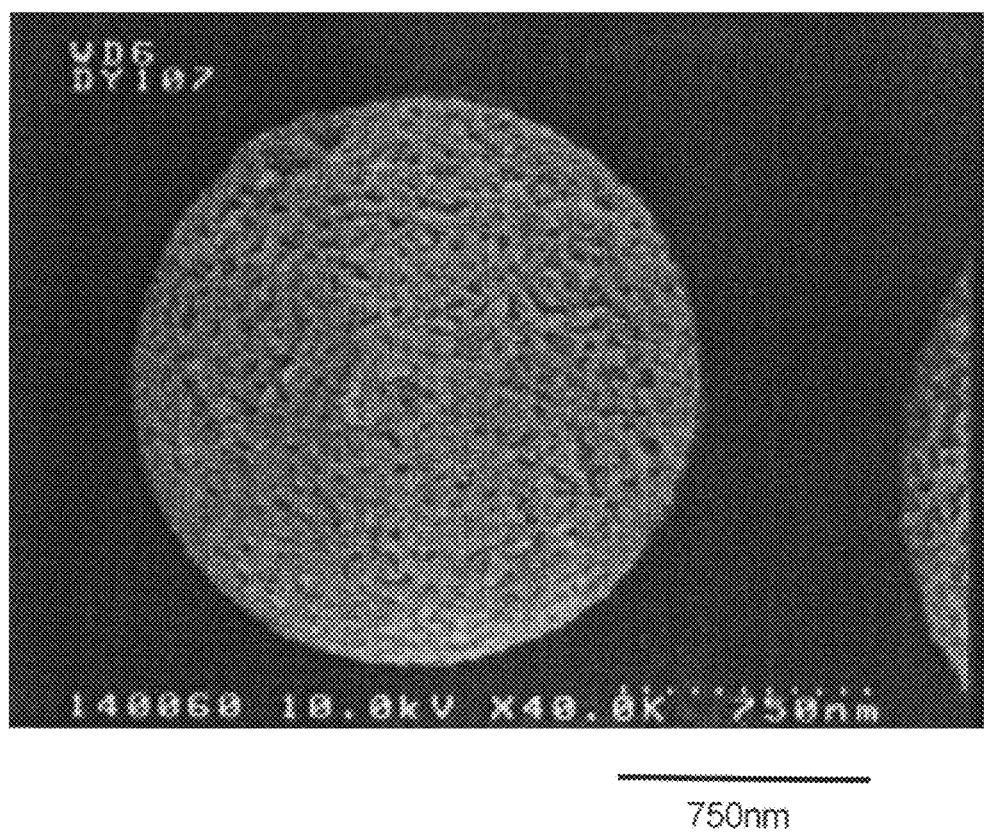
FIG. 4 is a SEM image of the deodorant particles obtained in Example 3.

In a mixed organic solvent of 112.5 g of octane and 37.5 g of toluene were dissolved 100 g of a monomer mixture (styrene/divinylbenzene/2-vinylpyridine=12.5/75/12.5) and 3 g of lauroyl peroxide. The monomer mixture was put into a polymerization vessel together with 500 g of water containing 1.5 g of sodium N-stearyltaurate. The solubility parameters of the monomer mixture and the organic solvent were 9.32 and 7.92, respectively, making a difference of 1.40. The mixture in the vessel was agitated by means of a homogenizer at 10000 rpm for 5 minutes to form an emulsion, which was heated at 85° C. for 4 hours and then at 95° C. for 3 hours while stirring at 200 rpm to cause polymerization. After the reaction mixture was filtered, the filter cake was dried to give deodorant particles with a yield of 91%. The SEM image of the resulting deodorant particles is shown in FIG. 4.

Example 4

In a mixed organic solvent of 225 g of octane and 75 g of toluene were dissolved 100 g of a monomer mixture (styrene/divinylbenzene/2-vinylpyridine=12.5/75/12.5) and 3 g of lauroyl peroxide in a polymerization vessel. The solubility parameters of the monomer mixture and the organic solvent were 9.32 and 7.92, respectively, making a difference of 1.40. The monomer mixture was heated at 85° C. for 4 hours and then at 95° C. for 3 hours to cause polymerization. The reaction mixture was dried to give deodorant particles in a yield of 80%.

Example 5

In a mixed organic solvent of 180 g of heptane and 120 g of toluene were dissolved 100 g of a monomer mixture (divinylbenzene/2-vinylpyridine=75/25) and 3 g of lauroyl peroxide. The solubility parameters of the monomer mixture and the organic solvent were 9.37 and 7.99, respectively, making a difference of 1.38. The monomer mixture was heated in a polymerization vessel at 70° C. for 6 hours, followed by addition of 3 g of lauroyl peroxide dissolved in 20 g of toluene. The heating was further continued at the same temperature for an additional 4 hour period to complete polymerization. The reaction mixture was dried to give deodorant particles in a yield of 98%.

Example 6

A hundred grams of the deodorant particles prepared in Example 3 were added to a solution of 0.5 g of silver nitrate in 1000 g of ethanol, followed by stirring at room temperature for 6 hours. The mixture was filtered, and the filter cake was washed with water to obtain deodorant particles having silver nitrate supported thereon.

Example 7

Deodorant particles were obtained in the same manner as in Example 6, except for replacing the deodorant particles of Example 3 with those obtained in Example 4.

Example 8

A hundred grams of the deodorant particles prepared in Example 4 were added to a solution of 10 g of silver nitrate in 1000 g of ethanol, followed by stirring at room temperature for 6 hours. The mixture was filtered, and the filter cake was washed with water to obtain deodorant particles having silver nitrate supported thereon.

Example 9

In a mixed organic solvent of 60 g of dichlorobenzene and 90 g of toluene were dissolved 100 g of a monomer mixture (styrene/divinylbenzene/2-vinylpyridine=12.5/75/12.5) and 3 g of lauroyl peroxide. The monomer mixture was put in a polymerization vessel together with 500 g of water containing 1.5 g of sodium N-stearyltaurate. The solubility parameters of the monomer mixture and the organic solvent were 9.32 and 9.53, respectively, making a difference of 0.21. The mixture in the vessel was agitated by means of a homogenizer at 10000 rpm for 5 minutes to form an emulsion, which was heated at 85° C. for 4 hours and then at 95° C. for 3 hours while stirring at 200 rpm to cause polymerization. The reaction mixture was filtered to remove water and the organic solvent, and the filter cake was dried to give deodorant particles with a yield of 98%.

Example 10

In a mixed organic solvent of 30 g of toluene and 20 g of t-butanol were dissolved 100 g of a monomer mixture (divinylbenzene/2-vinylpyridine=75/25) and 3 g of lauroyl peroxide. The monomer mixture was put into a polymerization vessel together with 500 g of water containing 1.5 g of sodium N-stearyltaurate. The solubility parameters of the monomer mixture and the organic solvent were 9.37 and 9.40, respectively, making a difference of 0.03. The mixture in the vessel was agitated by means of a homogenizer at 10000 rpm for 5 minutes to form an emulsion, which was heated at 55° C. for 4 hours and then at 65° C. for 3 hours while stirring at 200 rpm to cause polymerization. The reaction mixture was filtered to remove water and the organic solvent, and the filter cake was dried to give deodorant particles with a yield of 90%.

Example 11

In a mixed organic solvent of 117.6 g of toluene and 176.5 g of heptane were dissolved 588.3 g of a monomer mixture (divinylbenzene/2-vinylpyridine=75/25) and 11.0 g of lauroyl peroxide. The monomer mixture was put into a polymerization vessel together with 1600 g of an aqueous solution containing 15.6 g of polyvinyl alcohol (Gosenol EG-30, from The Nippon Synthetic Chemical Industry Co., Ltd.). The solubility parameters of the monomer mixture and the organic solvent were 9.37 and 7.92, respectively, making a difference of 1.45. The mixture in the vessel was agitated by means of a homogenizer at 10000 rpm for 5 minutes to form an emulsion, which was heated at 70° C. for 8 hours while stirring at 128 rpm to conduct polymerization. The reaction mixture was dried to remove water and the organic solvent. To 100 g of the resulting particles were added 263 g of water, 23 g of isopropyl alcohol, 0.5 g of silver acetate, and 1.0 g of ammonium sulfate, followed by stirring at room temperature for 1 hour. The mixture was filtered, and the filter cake was dried to yield deodorant particles.

Example 12

In 296 g of heptane were dissolved 592.7 g of a monomer mixture (divinylbenzene/2-vinylpyridine=75/25) and 11.0 g of 2,2'-azobis(2,4-dimethylvaleronitrile) (V-65B, from Wako Pure Chemical Industries, Ltd.). The monomer mixture was put into a polymerization vessel together with 1600 g of an aqueous solution of 15.6 g of polyvinyl alcohol (Gosenol EG-30, from The Nippon Synthetic Chemical Industry Co., Ltd.). The solubility parameters of the monomer mixture and the organic solvent were 9.37 and 7.40, respectively, making a difference of 1.97. The mixture in the vessel was agitated by means of a homogenizer at 5000 rpm for 10 minutes to form an emulsion, which was heated at 60° C. for 6 hours while stirring at 128 rpm to cause polymerization. To the reaction mixture was added 750 g of 1-butanol, followed by drying under reduced pressure to remove water and the organic solvent. To 100 g of the resulting particles were added 263 g of water, 23 g of isopropyl alcohol, 0.5 g of silver acetate, and 1.0 g of citric acid, followed by stirring at room temperature for 1 hour. The mixture was filtered, and the filter cake was dried to provide deodorant particles.

Comparative Example 1

In a mixed organic solvent of 112.5 g of octane and 37.5 g of toluene were dissolved 100 g of a monomer mixture (styrene/divinylbenzene=25/75) and 3 g of lauroyl peroxide. The monomer mixture was put into a polymerization vessel together with 500 g of water containing 1.5 g of sodium N-stearyltaurate. The solubility parameters of the monomer mixture and the organic solvent were 9.27 and 7.92, respectively, making a difference of 1.35. The mixture in the vessel was agitated by means of a homogenizer at 10000 rpm for 5 minutes to form an emulsion, which was heated at 85° C. for 4 hours and then at 95° C. for 3 hours while stirring at 200 rpm to cause polymerization. The reaction mixture was filtered to remove water and the organic solvent, and the filter cake was dried to give deodorant particles with a yield of 90%.

Comparative Example 2

Non-crosslinked polystyrene particles (general-purpose grade GP-1B, from Toyo Styrene Co., Ltd.) was used.

Comparative Example 3

In 300 g of ethanol were dissolved 100 g of a monomer mixture (styrene/divinylbenzene/2-vinylpyridine=12.5/75/12.5) and 3 g of lauroyl peroxide. The monomer mixture was put into a polymerization vessel together with 500 g of water containing 1.5 g of sodium N-stearyltaurate. The solubility parameters of the monomer mixture and the organic solvent were 9.32 and 12.30, respectively, making a difference of 2.98. The mixture in the vessel was heated at 85° C. for 4 hours and then at 95° C. for 3 hours to conduct polymerization. The reaction mixture was filtered to remove water and the organic solvent, and the filter cake was dried to give deodorant particles in a yield of 96%.

and the surface area was divided by the weight of the sample to give the specific surface area.

Silver Ion Content:

The silver ion content in the deodorant particles having silver nitrate or silver acetate supported thereon was measured by monochromatic excitation energy dispersive X-ray fluorescence spectrometry (EDX).

Average Particle Size:

The deodorant particles were crushed in a coffee mill and dispersed in hexane. The volume average particle size of the dispersed particles was measured with a Coulter counter (from Coulter Corp.).

TABLE 1

| | | Example | | | | | | | |
|---|---|---|---|---|---|---|---|---|---|
| | | 1 | 2 | 3 | 4 | 5 | 6 | 7 | 8 |
| Particle | St | 35 | 25 | 12.5 | 12.5 | 0 | 12.5 | 12.5 | 12.5 |
| Composition (%) | DVB | 60 | 70 | 75 | 75 | 75 | 75 | 75 | 75 |
| | 2-Vpy | 5 | 5 | 12.5 | 12.5 | 25 | 12.5 | 12.5 | 12.5 |
| SP of Monomer Mixture | | 9.28 | 9.29 | 9.32 | 9.32 | 9.37 | 9.32 | 9.32 | 9.32 |
| SP of Organic Solvent | | 7.88 | 7.88 | 7.92 | 7.92 | 7.99 | 7.92 | 7.92 | 7.92 |
| Absolute Difference of SP between Monomer Mixture and Organic Solvent | | 1.44 | 1.41 | 1.40 | 1.40 | 1.38 | 1.40 | 1.40 | 1.40 |
| Polymerization Method | | ppt. | ppt. | ems. | ppt. | ppt. | ems. | ppt. | ppt. |
| Avg. Particle Size (μm) | | 16.5 | 21.4 | 7.3 | 39.7 | 53.6 | 7.3 | 39.7 | 39.7 |
| Ag Ion Content (%) | | 0 | 0 | 0 | 0 | 0 | 0.27 | 0.28 | 3.7 |
| BET Specific Surface Area (m$^2$/g) | | 313 | 431 | 351 | 428 | 386 | 416 | 486 | 363 |

| | | Example | | | | Comp. Example | | |
|---|---|---|---|---|---|---|---|---|
| | | 9 | 10 | 11 | 12 | 1 | 2 | 3 |
| Particle | St | 12.5 | 0 | 0 | 0 | 25 | 100 | 12.5 |
| Composition (%) | DVB | 75 | 75 | 75 | 75 | 75 | 0 | 75 |
| | 2-Vpy | 12.5 | 25 | 25 | 25 | 0 | 0 | 12.5 |
| SP of Monomer Mixture | | 9.32 | 9.37 | 9.37 | 9.37 | 9.27 | 9.27 | 9.32 |
| SP of Organic Solvent | | 9.53 | 9.40 | 7.92 | 7.40 | 7.92 | — | 12.3 |
| Absolute Difference of SP between Monomer Mixture and Organic Solvent | | 0.21 | 0.03 | 1.45 | 1.97 | 1.35 | — | 2.98 |
| Polymerization Method | | ems. | ems. | ems. | ems. | ems. | com. product | ppt. |
| Avg. Particle Size (μm) | | 4.8 | 5.3 | 7.9 | 23.5 | 5.2 | — | 128 |
| Ag Ion Content (%) | | 0 | 0 | 0.33 | 0.25 | 0 | 0 | 0 |
| BET Specific Surface Area (m$^2$/g) | | 401 | 18.3 | 226 | 234 | 427 | 0.17 | 2.0 |

Abbreviation:
SP: solubility parameter
ppt: precipitation polymerization
ems.: emulsion polymerization
com. product: commercial product The deodorant particles obtained in Examples 1 through 12 and Comparative Examples 1 through 3 were measured for BET specific surface area, silver ion content, and average particle size in accordance with the methods described below. The results of the measurements are shown in Table 1.

BET Specific Surface Area:

The BET specific surface area of the deodorant particles was measured by the BET one-point method using Flowsorb 2300 (from Shimadzu Corp.) and a nitrogen/helium (30/70 by volume) mixed adsorbate gas. A sample was pretreated by making the adsorbate gas to flow at 120° C. for 10 minutes. Thereafter, a cell having the sample was cooled with liquid nitrogen. After completion of adsorption, the temperature was raised to room temperature. The surface area of the sample was obtained from the amount of released nitrogen, In Table 1, St means styrene, DVB means divinylbenzene, and 2-Vpy means 2-vinylpyridine.

Test Example 1

The deodorant particles obtained in Examples 1 to 3, 5, 6, and 9 and Comparative Examples 1 and 3 were evaluated in terms of p-cresol deodorization rate in accordance with the method below. The results obtained are shown in Table 2.

Measurement of p-Cresol Deodorization Rate

In a one-liter polyethylene bottle were sealed 12 μl of p-cresol and 10 mg of the deodorant particles. One hour later, the p-cresol concentration in the bottle was measured with a gas detector tube (No. 61, from Gas Tech K.K.). A p-cresol deodorization rate was obtained according to the following equation using the value measured without the deodorant particles as a blank concentration.

$$\text{Deodorization rate}(\%) = [(\text{blank concentration} - \text{residual p-cresol concentration})/\text{blank concentration}] \times 100$$

TABLE 2

|  | Example | | | | | | Comp. Example | |
|---|---|---|---|---|---|---|---|---|
|  | 1 | 2 | 3 | 5 | 6 | 9 | 1 | 3 |
| p-Cresol Deodorization Rate (%) | 58 | 67 | 76 | 82 | 81 | 77 | 52 | 32 |

Test Example 2

The deodorant particles obtained in Examples 3 and 6 and Comparative Examples 1 and 2 were evaluated for rate of deodorization against phenol, dimethyl disulfide and pyrrole in accordance with the method described below. The results obtained are shown in Table 3.

Phenol, Dimethyl Disulfide and Pyrrole Deodorization Rate

An aqueous solution was prepared from 484.9 g of ion exchanged water, 9.7 g of urea, 3.98 g of sodium chloride, 0.55 g of magnesium sulfate, 0.31 g of calcium chloride, 0.99 g of potassium sulfate, and 0.02 g of a nonionic surface active agent (Emulgen, from Kao Corp.). Each of malodorous compounds, phenol, dimethyl sulfide, and pyrrole, was diluted with the aqueous solution to a concentration of 20 ppm. To 3 ml of the thus prepared malodorous compound solution were added 30 mg of the test deodorant particles, followed by stirring for 3 minutes, followed by centrifugation. To a 1 ml portion of the aqueous phase were added 2 ml of diethyl ether and 0.5 g of sodium chloride, followed by stirring for 2 minutes, followed by centrifugation. The malodorous compound concentration of the oily phase was measured by gas chromatography. The malodorous compound deodorization rate was calculated from equation below using the value measured without the deodorant particles as a blank concentration.

$$\text{Deodorization rate}(\%) = [(\text{blank concentration} - \text{residual malodorous compound concentration})/\text{blank concentration}] \times 100$$

TABLE 3

|  | Example | | Comp. Example | |
|---|---|---|---|---|
|  | 3 | 6 | 1 | 2 |
| Phenol Deodorization Rate (%) | 63 | 73 | 27 | 0 |
| Dimethyl Disulfide Deodorization Rate (%) | 97 | 96 | 18 | 31 |
| Pyrrole Deodorization Rate (%) | 33 | 33 | 21 | 0 |

Test Example 3

The deodorant particles obtained in Examples 3 to 4, 6 to 8, and 10 to 12 and Comparative Examples 1 and 2 were evaluated for deodorizing performance against the odor of urine in accordance with the method described below. The results obtained are shown in Table 4.

Evaluation of Deodorizing Performance Against Urine Odor

Fifty milligrams of the test deodorant particles were put in a 30 ml Erlenmeyer flask containing 5 g of human urine and 250 mg of a superabsorbent polymer (Aqualic CAW4S, from Nippon Shokubai Co., Ltd.), and the flask was stoppered. After 20 minute, the intensity of urine odor from the flask was organoleptically scored by three experts in 0.5 increments on a scale of 0 (odorless) to 5 (extremely intense). The average of the scores by the three was rounded to the nearest 0.5 increment (for example, 2.66 was rounded to 2.5, and 3.13 to 3.0). The odor intensity of a blank (without any deodorant particles) was scored 3.0.

TABLE 4

|  | Example | | | | | | | | Comp. Example | |
|---|---|---|---|---|---|---|---|---|---|---|
|  | 3 | 4 | 6 | 7 | 8 | 10 | 11 | 12 | 1 | 2 |
| Urine Odor Intensity | 2.0 | 2.0 | 1.5 | 1.5 | 1.5 | 2.0 | 1.0 | 1.0 | 2.5 | 3.0 |

Test Example 4

The deodorant particles obtained in Examples 3 to 4 and 6 to 8 and Comparative Examples 1 and 2 were evaluated for deodorizing performance against the odor of feces in accordance with the method described below. The results obtained are shown in Table 5.

Evaluation of Deodorizing Performance Against Fecal Odor

Three grams of human feces was put in a plastic circular container of 5 cm in diameter. The container was placed in a 3 liter bag and allowed to stand for 30 minutes. Twenty milliliters of air was withdrawn from the bag using a syringe and transferred into another bag containing 10 mg of the test deodorant particles (placed in a 45 mm diameter petri dish). Thirty minutes later, the intensity of the fecal odor was organoleptically scored by 3 experts in 0.5 increments on a scale of 0 (odorless) to 5 (extremely intense). The average of the scores by the three was rounded to the nearest 0.5 increment (for example, 2.66 was rounded to 2.5, and 3.13 to 3.0). The odor intensity of a blank (without any deodorant particles) was scored 3.0.

TABLE 5

|  | Example | | | | | Comp. Example | |
|---|---|---|---|---|---|---|---|
|  | 3 | 4 | 6 | 7 | 8 | 1 | 2 |
| Fecal Odor Intensity | 2.0 | 2.0 | 1.0 | 1.0 | 1.0 | 2.5 | 3.0 |

Test Example 5

The deodorant particles obtained in Examples 3 to 4 and 6 to 8 and Comparative Examples 1 and 2 were evaluated for deodorizing performance against the odor of tobacco in accordance with the method described below. The results obtained are shown in Table 6.

Evaluation of Deodorizing Performance Against Tobacco Odor

Tobacco of 1 cm of a cigarette (Mild Seven Original) was burnt in a 1 liter separable flask and allowed to stand for 30 minutes. Two milliliters of air was withdrawn from the flask using a syringe and sealed into a 50 ml glass bottle containing 0.1 g of the test deodorant particles. Fifteen minutes later, the intensity of the tobacco odor was organoleptically scored by 3 experts in 0.5 increments on a scale of 0 (odorless) to 5 (extremely intense). The average of the scores by the three was rounded to the nearest 0.5 increment. The odor intensity of a blank (without any deodorant particles) was scored 3.0.

TABLE 6

|  | Example | | | | | Comp. Example | |
|---|---|---|---|---|---|---|---|
|  | 3 | 4 | 6 | 7 | 8 | 1 | 2 |
| Tobacco Odor Intensity | 2.0 | 2.0 | 1.5 | 1.5 | 1.5 | 2.5 | 3.0 |

Example 13

A slurry having a pulp concentration of 2% was prepared from the deodorant particles obtained in Example 3, softwood kraft pulp having been beaten to a CSF of 200 ml, a wet-strength additive (WS4024, from Seiko PMC Corp.), and a polyacrylamide flocculant (Accoflock A95, from Mitsui Aqua Polymer, Inc.). The concentrations of the deodorant particles, wet-strength additive, and polymer flocculant were 10%, 0.5%, and 0.1%, respectively, based on the pulp content. The slurry was dewatered and formed into a 25 cm by 25 cm sheet by manual papermaking. The sheet was cut into 20 cm by 20 cm in size to obtain a particle-containing pulp sheet. The particle-containing pulp sheet had a grammage of 30 g/m² and contained 50 mg of the deodorant particles.

Evaluation of Deodorizing Performance—Methylmercaptan Deodorization Rate (%):

In a 500 ml Erlenmeyer flask with ground glass stopper was put a piece of the particle-containing pulp sheet sampled weighing 0.1 g. Into the flask was introduced methylmercaptan gas having a controlled concentration to result in an initial concentration of 3.5 ppm. Ten minutes later, the methylmercaptan gas concentration in the flask was measured with a gas detector tube (Methylmercaptans 70L, from Gas Tech K.K.) to obtain a deodorization rate (measured value/initial concentration×100). A higher deodorization rate indicates higher deodorizing performance.

Example 14

A slurry having a pulp concentration of 2% was prepared from the deodorant particles obtained in Example 6, softwood kraft pulp having been beaten to a CSF of 200 ml, a wet-strength additive (WS4024, from Seiko PMC Corp.), and a polyacrylamide flocculant (Accoflock A95, from Mitsui Aqua Polymer, Inc.). The concentrations of the deodorant particles, wet-strength additive, and polymer flocculant were 10%, 0.5%, and 0.1%, respectively, based on the pulp content. The slurry was formed into a 25 cm by 25 cm sheet by manual papermaking. The sheet was cut into 20 cm by 20 cm in size to obtain a particle-containing pulp sheet. The particle-containing pulp sheet had a grammage of 30 g/m² and contained 50 mg of the deodorant particles.

Example 15

A hundred grams of the deodorant particles obtained in Example 10 were treated in 100 g of ethanol having 0.5 g of silver nitrate dissolved therein at room temperature for 6 hours. The particles were collected by filtration and washed with water to give deodorant particles having silver nitrate supported thereon. The resulting deodorant particles had a BET specific surface area of 18.3 m²/g and a silver ion content of 0.14%. A particle-containing pulp sheet was made in the same manner as in Example 13, except that those deodorant particles having silver nitrate supported thereon were used. The particle-containing pulp sheet had a grammage of 30 g/m² and contained 50 mg of the deodorant particles.

Comparative Example 4

A particle-containing sheet was made in the same manner as in Example 13, except for replacing the deodorant particles employed in Example 13 with particles prepared by Comparative Example 1.

Comparative Example 5

A particle-containing sheet was made in the same manner as in Example 13, except for replacing the deodorant particles employed in Example 13 with particles employed in Comparative Example 2.

The sheets obtained in Examples 13 to 15, and Comparative Examples 4 and 5 were evaluated by the above-described method of evaluation. The results obtained are shown in Table 7 below.

TABLE 7

|  | Example 13 | Example 14 | Example 15 | Compara. Example 4 | Compara. Example 5 |
|---|---|---|---|---|---|
| Deodorization Rate (%) | 42 | 94 | 80 | 8 | 3 |

As is apparent from Table 7, the sheets of Examples 13 to 15 achieve greatly increased deodorization rates, which indicate greatly improved deodorizing performance, as compared with those of Comparative Examples 4 and 5.

Example 16-1

An absorbent article of the structure illustrated in FIG. 4 was made using the deodorant particles obtained in Example 6. In more detail, a pulp fiber aggregate 13 weighing 2 g was prepared. Over the fiber aggregate 13 were spread 20 mg of the deodorant particles and 2 g of superabsorbent polymer particles, and the particle-containing fiber aggregate 13 was wrapped in paper 14 (grammage: 15 g/m²) to make an absorbent member 10. The absorbent member 10 was sealed in between a topsheet 11 (air-through nonwoven fabric weighing 25 g/m²) and a backsheet 12 (moisture permeable film weighing 40 g/m²) to assemble an absorbent article.

Example 16-2

An absorbent article was made in the same manner as in Example 16-1, except for increasing the amount of the deodorant particles to 40 mg.

Example 16-3

An absorbent article was made in the same manner as in Example 16-1, except for increasing the amount of the deodorant particles to 78 mg.

Example 17-1

A hundred grams weighed out of the deodorant particles obtained in Example 4 were added to a solution of 0.5 g of silver nitrate in 1000 g of ethanol. The mixture was stirred at room temperature for 6 hours whereby silver nitrate was supported on the deodorant particles. The mixture was filtered, and the filter cake was washed with water to obtain silver nitrate-containing deodorant particles. The resulting deodorant particles had a BET specific surface area of 486 m$^2$/g and a silver ion content of 0.28%. An absorbent article was assembled in the same manner as in Example 16-1, except for using the thus prepared deodorant particles.

Example 17-2

An absorbent article was made in the same manner as in Example 17-1, except for increasing the amount of the deodorant particles to 40 mg.

Example 17-3

An absorbent article was made in the same manner as in Example 17-1, except for increasing the amount of the deodorant particles to 78 mg.

Comparative Examples 6-1 to 6-3

Absorbent articles were made in the same manner as in Examples 16-1 to 16-3, except for replacing the deodorant particles with the same amount of zinc chloride-activated carbon as in the respective Examples.

Comparative Example 7

An absorbent article was made in the same manner as in Example 16-3, except for replacing the deodorant particles with the same amount of particles which were obtained in Comparative Example 1.

Comparative Example 8

An absorbent article was made in the same manner as in Example 16-3, except for replacing the deodorant particles with the particles employed in Comparative Example 2.

Comparative Example 9

An absorbent article was made in the same manner as in Example 16-1, except for using no deodorant particles.

Evaluation of Deodorizing Performance

Five hundred milliliters of human urine were collected from five male adults (100 ml from each person). A 30 g portion of the urine sample was poured on each of the absorbent articles obtained in Examples and Comparative Examples, and immediately thereafter, the absorbent article was put into a 1.2-liter air-tight container (Tight Box No. 3, from Chopla Kogyo K.K.). Sixty minutes later, each container was opened, and a panel of 5 members smelled the contents and evaluated the odor based on the following scoring system: 0.0=odorless; 1.0=perceptible but unidentifiable; 2.0=odorous of urine; 3.0=strongly odorous of urine. An average score given by the panel was taken as an organoleptic value representing the strength of odor. The smaller the value, the weaker the odor. The same human urine was used in all the Examples and the Comparative Examples. The results obtained are shown in Table 8.

TABLE 8

|  | Odor |
|---|---|
| Example 16-1 | 1.7 |
| Example 16-2 | 1.3 |
| Example 16-3 | 1.0 |
| Example 17-1 | 1.5 |
| Example 17-2 | 1.3 |
| Example 17-3 | 1.1 |
| Comp. Example 6-1 | 1.7 |
| Comp. Example 6-2 | 1.3 |
| Comp. Example 6-3 | 1.0 |
| Comp. Example 7 | 1.7 |
| Comp. Example 8 | 2.8 |
| Comp. Example 9 | 3.0 |

As is apparent from Table 8, the absorbent articles of the present invention (Examples 16-1 to 16-3 and 17-1 to 17-3) having the deodorant polymer particles exhibit equal or superior deodorizing properties to the comparative ones using the existing activated carbon deodorizer (Comparative Examples 6-1 to 6-3). The activated carbon deodorizer is black, whilst the deodorant particles used in the present invention are white and are therefore particularly suited for use in personal care absorbent articles. It is also seen that polymer particles containing no vinyl monomer unit having a heteroaromatic ring (Comparative Example 7) and polymer particles with a small BET specific surface area (Comparative Example 8) have low deodorizing effects.

Then, the absorbent articles of Examples 16-1 to 16-3 were compared with those obtained in Examples 18-1 to 18-3 given below to examine any difference in deodorizing effect attributed to a configurational difference.

Example 18-1

A particle-containing sheet was formed by a wet papermaking technique as follows using the same deodorant particles as prepared in Example 16-1. A slurry having a pulp concentration of 2% was prepared from the deodorant particles, softwood kraft pulp having been beaten to a CSF of 200 ml, a wet-strength additive (WS4024, from Seiko PMC Corp.), and a polyacrylamide flocculant (Accoflock A95, from Mitsui Aqua Polymer, Inc.). The concentrations of the deodorant particles, wet-strength additive, and polymer flocculant were 3%, 0.5%, and 0.1%, respectively, based on the pulp content. The slurry was dewatered and formed into a 25 cm by 25 cm particle-containing pulp sheet by manual papermaking. The particles-containing pulp sheet had a grammage of 30 g/m$^2$. The sheet was cut into a 20 cm square to provide a particle-containing sheet, which contained 20 mg of the deodorant particles.

An absorbent article of the structure illustrated in FIG. 5 was made using the resulting particle-containing sheet as follows. A pulp fiber aggregate 13 weighing 2 g was prepared as a fibrous material constituting an absorbent member 10. Over the fiber aggregate 13 were spread 2 g of superabsorbent polymer particles, and the superabsorbent polymer-containing fiber aggregate 13 was wrapped in the particle-containing sheet 1 and further wrapped in paper 14 to make an absorbent member 10. The absorbent member 10 was sandwiched in between a topsheet 11 and a backsheet 12 to assemble an absorbent article in the same manner as in Example 16-1 unless otherwise noted.

Example 18-2

An absorbent article was assembled in the same manner as in Example 18-1, except for increasing the concentration of the deodorant particles in the slurry to 6% based on the pulp. The amount of the deodorant particles in the particle-containing sheet 1 was found to be 36 mg.

Example 18-3

An absorbent article was made in the same manner as in Example 16-1, except for increasing the concentration of the deodorant particles to 10% based on the pulp. The amount of the deodorant particles in the particle-containing sheet 1 was found to be 60 mg.

The absorbent articles obtained in Examples 16-1 to 16-3 were evaluated for deodorizing effect in the same manner as in Examples 18-1 to 18-3. The results obtained are shown in Table 8 above and Table 9 below.

TABLE 9

|  | Odor |
| --- | --- |
| Example 18-1 | 1.6 |
| Example 18-2 | 1.3 |
| Example 18-3 | 1.2 |

Comparison between Tables 8 and 9 proves that the absorbent articles of the present invention achieve the same level of deodorization whichever of the configurations is taken; (a) a configuration in which the deodorant particles are supported directly on the fibers constituting the absorbent member (Examples 16-1 to 16-3) and (b) a configuration in which the deodorant particles are disposed in the form of a particle-containing sheet (Examples 18-1 to 18-3).

Example 19

An absorbent article was made in the same manner as in Example 16-1, except that the deodorant particles having silver nitrate supported thereon obtained in Example 15 were used and that the amount of those deodorant particles was changed to 50 mg. The absorbent article was evaluated in the same manner as in Examples 16-1 to give the results shown in Table 10.

TABLE 10

|  | Odor |
| --- | --- |
| Example 19 | 1.3 |

INDUSTRIAL APPLICABILITY

As described in detail, the deodorant particles of the present invention exhibit excellent deodorizing performance against malodors irrespective of the properties of the malodors, particularly against neutral to weakly acidic odors. The deodorizing effects of the deodorant particles are markedly enhanced by having a metal ion supported on the heteroaromatic ring of the polymer particles. The deodorant particles having the metal ion exhibit very high deodorizing effects on composite odors of many malodorous components, such as the odor of human or animal (cats and dogs) urine and feces, the odor of tobacco, odors from drain pipes, and the odor of cooking, especially the odors of human or animal (cats and dogs) urine and feces and tobacco.

The deodorant fibrous product and the absorbent article according to the present invention contain deodorant particles that exhibit excellent deodorizing performance irrespective of the properties of malodors to be removed and therefore achieve superior deodorization. The absorbent article of the invention is capable of effectively removing the unpleasant odor from body exudates.

The invention claimed is:

1. A deodorant particle having a BET specific surface area of $10 \, m^2/g$ or more that is obtained by copolymerizing monomers comprising a crosslinkable vinyl monomer and a vinyl monomer having a heteroaromatic ring,
    wherein the deodorant particle further contains a metal ion, and
    wherein a proportion of the crosslinkable vinyl monomer in the monomer system is from 20 to 98% by mass;
    wherein the crosslinkable vinyl monomer is selected from the group consisting of divinylbenzene, trivinylbenzene and ethylene glycol di(meth)acrylate, and wherein the vinyl monomer having a heteroaromatic ring is selected from the group consisting of 2-vinylpyridine, 4-vinylpyridine, 1-vinylimidazole and 2-vinylpyrimidine.

2. The deodorant particle according to claim 1, wherein the deodorant particle is obtained by oil-in-water emulsion polymerization or precipitation polymerization.

3. A process of producing the deodorant particle according to claim 1, which comprises the steps of copolymerizing monomers comprising a crosslinkable vinyl monomer and a vinyl monomer having a heteroaromatic ring by oil-in-water emulsion polymerization or precipitation polymerization using an organic solvent whose solubility parameter is different from that of the monomers by an absolute difference of 0 to 2.0, and subsequently bringing a particle obtained by the polymerization into contact with a solvent having a metal salt dissolved therein to support a metal ion on the particle.

4. A deodorant fibrous product comprising the deodorant particle recited in claim 1.

5. The deodorant fibrous product according to claim 4, which is in the form of a sheet, a broken piece of a sheet, granule, or three-dimensional molding.

6. An absorbent article comprising the deodorant particle recited in claim 1.

7. The absorbent article according to claim 6, comprising a topsheet, a backsheet, an absorbent member interposed between the topsheet and the backsheet, and
    the deodorant particle supported on fibers which constitute the absorbent member.

8. The absorbent article according to claim 6, comprising a topsheet, a backsheet, an absorbent member interposed between the topsheet and the backsheet, and
    a particle-containing sheet in which the deodorant particle and a fibrous material are bonded to each other, the particle-containing sheet being disposed between the topsheet and the absorbent member, or within the absorbent member, or between the absorbent member and the backsheet.

9. The absorbent article according to claim 8, wherein the particle-containing sheet is obtained by a wet papermaking technique.

* * * * *